United States Patent
Behnke

(10) Patent No.: US 9,943,285 B1
(45) Date of Patent: Apr. 17, 2018

(54) DISPOSABLE ISOLATION/PROTECTIVE COVER FOR STETHOSCOPES

(71) Applicant: Jeanette Behnke, High Springs, FL (US)

(72) Inventor: Jeanette Behnke, High Springs, FL (US)

(*) Notice: Subject to any disclaimer, the term of this patent is extended or adjusted under 35 U.S.C. 154(b) by 387 days.

(21) Appl. No.: 14/121,972

(22) Filed: Jul. 7, 2014

(51) Int. Cl.
- *A61B 7/02* (2006.01)
- *A61B 19/08* (2006.01)
- *A61B 1/00* (2006.01)

(52) U.S. Cl.
CPC .............. *A61B 7/02* (2013.01); *A61B 19/081* (2013.01); *A61B 1/00142* (2013.01)

(58) Field of Classification Search
CPC ...... A61B 7/02; A61B 1/00142; A61B 19/081
USPC .......................................................... 181/131
See application file for complete search history.

(56) References Cited

U.S. PATENT DOCUMENTS

| | | | | |
|---|---|---|---|---|
| 4,867,265 A * | 9/1989 | Wright | ..................... | A61B 7/02 181/131 |
| 5,466,898 A * | 11/1995 | Gilbert | ................... | A61B 46/10 181/131 |
| 5,486,659 A * | 1/1996 | Rosenbush | .............. | A61B 7/02 181/131 |
| 5,539,162 A * | 7/1996 | Tuttle | ..................... | A61B 46/10 181/131 |
| 5,564,431 A * | 10/1996 | Seward | ..................... | A61B 7/02 206/69 |
| D376,043 S * | 12/1996 | Rix | .............................. | D24/134 |
| 5,592,946 A * | 1/1997 | Eddy | ......................... | A61B 7/02 150/154 |
| 5,747,751 A * | 5/1998 | Weckerle | ............... | A61B 46/10 181/131 |
| 5,813,992 A * | 9/1998 | Henwood | ................ | A61B 7/02 374/E1.012 |
| 6,186,957 B1 * | 2/2001 | Milam | ..................... | A61B 7/02 600/528 |
| D455,254 S * | 4/2002 | Sanchez-Thomas | ........ | D24/134 |
| 6,520,639 B2 * | 2/2003 | Avner | ..................... | A61B 1/227 351/205 |
| 7,575,094 B1 * | 8/2009 | Rosenberg | ............... | A61B 7/00 181/131 |
| 7,614,477 B2 * | 11/2009 | Statner | ................... | A61B 46/10 181/131 |
| 7,647,648 B2 * | 1/2010 | Komorowski | ..... | A41D 13/0012 2/51 |
| 7,806,267 B2 * | 10/2010 | Pack-Walden | ....... | B65D 33/002 181/131 |
| 9,049,992 B2 * | 6/2015 | Burmeister | ............... | A61B 7/02 |
| 2002/0170771 A1 * | 11/2002 | Milam | ..................... | A61B 7/02 181/131 |
| 2009/0165186 A1 * | 7/2009 | Mijares | .............. | A41D 13/1236 2/83 |
| 2009/0288908 A1 * | 11/2009 | Giroux | ..................... | A61B 7/02 181/131 |

(Continued)

*Primary Examiner* — Jeremy Luks

(57) ABSTRACT

A disposable isolation/protective cover for a stethoscope comprising a bell, elongated connector body portion and two ear pieces wherein said isolation/protective cover is sealed on all sides except for the bottom permitting the stethoscope to be inserted therethrough; said cover material is made of acoustically transmitting and viral, bacterial and fluid impermeable material. A flap closes the stethoscope once inserted completely enclosing the stethoscope and preventing exposure of any kind.

3 Claims, 8 Drawing Sheets

(56) References Cited

U.S. PATENT DOCUMENTS

| | | | |
|---|---|---|---|
| 2013/0341223 A1* | 12/2013 | Fong | A61B 46/10 206/363 |
| 2016/0045266 A1* | 2/2016 | Deporto | A61B 19/026 53/469 |
| 2016/0287206 A1* | 10/2016 | Sud | A61B 7/02 |

* cited by examiner

DISPOSABLE ISOLATION/PROTECTIVE COVER FOR STETHOSCOPES

BACKGROUND OF THE INVENTION

1. Field of the Invention

The above said invention is a way of preventing contamination and transmission of infectious organisms and other biohazards to the stethoscope.

2. The Need and Care of Said Invention in the Health System

In the case of "total Isolation" patients single use stethoscopes are used however multiple stethoscopes are used by the staff at each shift. Since the plastic stethoscope cannot leave the isolation rooms visitors and other health care workers can contaminate the scope with a single touch. Cleaning of a personal stethoscope with an antibacterial cleaner is a way of cleaning the stethoscope however not a guaranteed method.

3. Problems with "Like" Covers

Many covers have been developed for the control of cross-contamination: U.S. Pat. Nos. 4,867,265; 5,486,659; 5,564,431; 5,813,992. These inventions are effective in preventing contact with patient skin however some parts of the stethoscope are exposed in one way or another. U.S. Pat. No. 6,186,957 forms a pouch with a closed distal end and an open proximal end, configured to receive the "bell" and connector portion of the stethoscope. It has a first flap and a second flap in the form of a "Y" shape for covering of the two bifurcated ear tubes. While this prevents contamination when examination of the patient the stethoscope cannot be removed from the cover without contamination. U.S. Patent No. US2002010771 entitled "Protective Cover for Stethoscope and dispensing assembly comprising same" is a cover in an elongated form, closed at the first end and fully or partially open at a second, opposite end to form an enclosed volume for retention of the head and elongate connector body of the stethoscope. Contamination can occur while removing the cover after use.

4. Key Issues in the Prevention of Contamination

Contamination and transmission of infectious has become a critical issue in hospitals and clinics all over the world. Health care workers are asked to keep contamination and transmission from occurring by using clean or sterile precautions on their equipment and from patient to patient contact. However, contamination and transmission still occur. The present invention can and will stop the spreading of any biohazards or viruses and such as well as save time with its fast and easy way of putting the cover on and off.

5. Ways to Display Present Invention

The present invention can be displayed in "pop-up" tissue box as the plastic gloves are packaged in. Also can be put in small plastic sealed bags one per use.

6. Cost Effective

Health Care Industry can save substantial monies as the cost of present invention costs pennies versus dollars to manufacture the plastic disposable ones.

SUMMARY OF THE INVENTION

The present invention is a single use protective/isolation cover for a stethoscope and other like items. The "Y" shape cover is sealed on all sides with an opening at the bottom. A flap folds under and over the front part of the cover after insertion completely sealing the stethoscope. Slits can be used to expose the ear tubes and the bell for "protective" use, however it is a total isolation system when needed. Material for the present invention will be OSHA approved i.e. material that is acoustically trans missive and impermeable to bacteria, viruses, biohazards and fluids. The sealing can be of heat, adhesive bonding, radio-frequency or any other type of sealing of bags of this kind. What this present invention offers is a quick and easy way to put on and remove the stethoscope or other like items without contamination.

DETAILED DESCRIPTION OF THE INVENTION

FIG. 1

Figure 1:
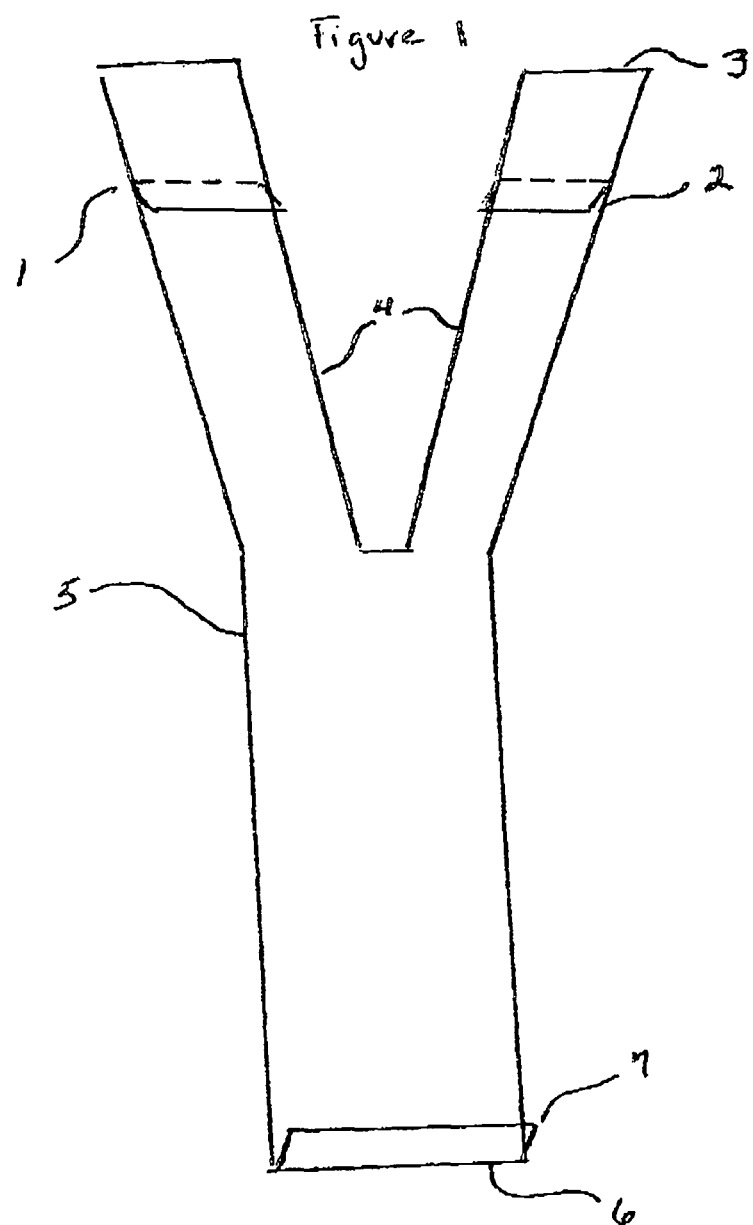
FIG. 1 is a perspective view of the disposable isolation/protective stethoscope cover according to an embodiment of the present invention.
Figure 2:
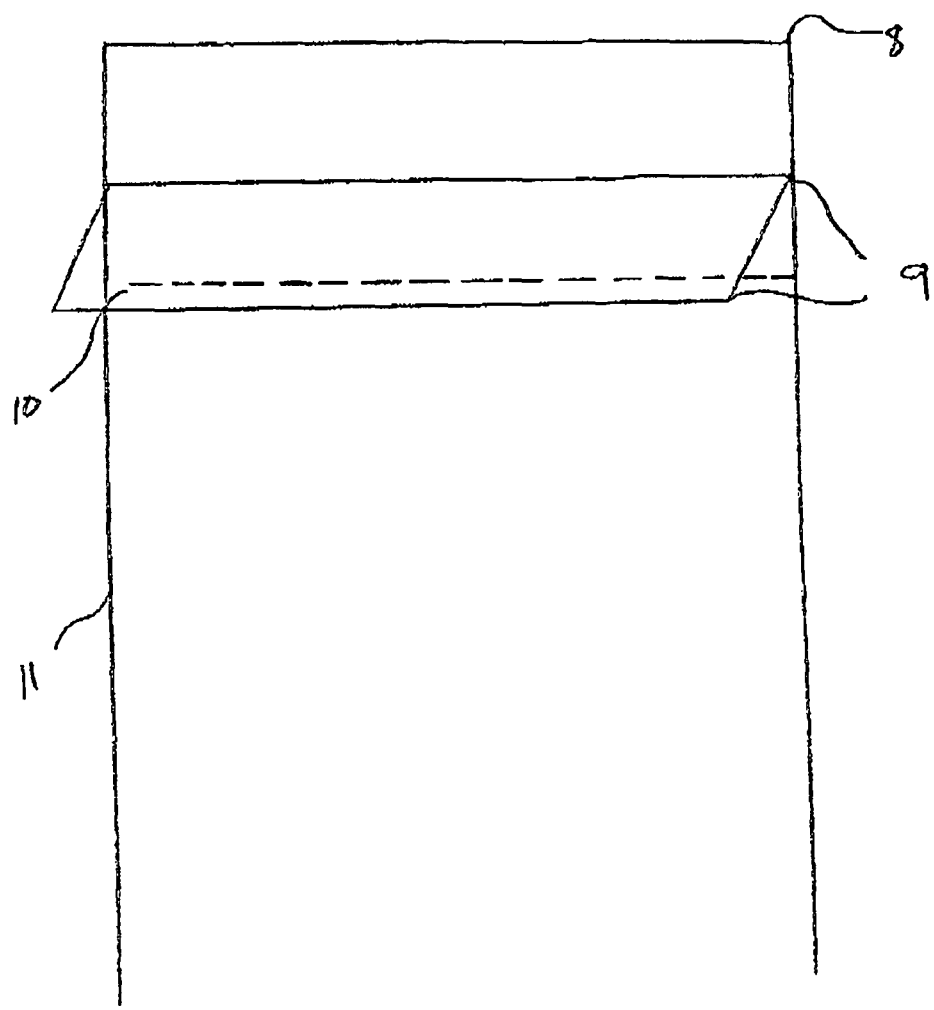
FIG. 2 is a perspective view of a flap for exposing stethoscope ear tubes according to an embodiment of the present invention.
Figure 3:
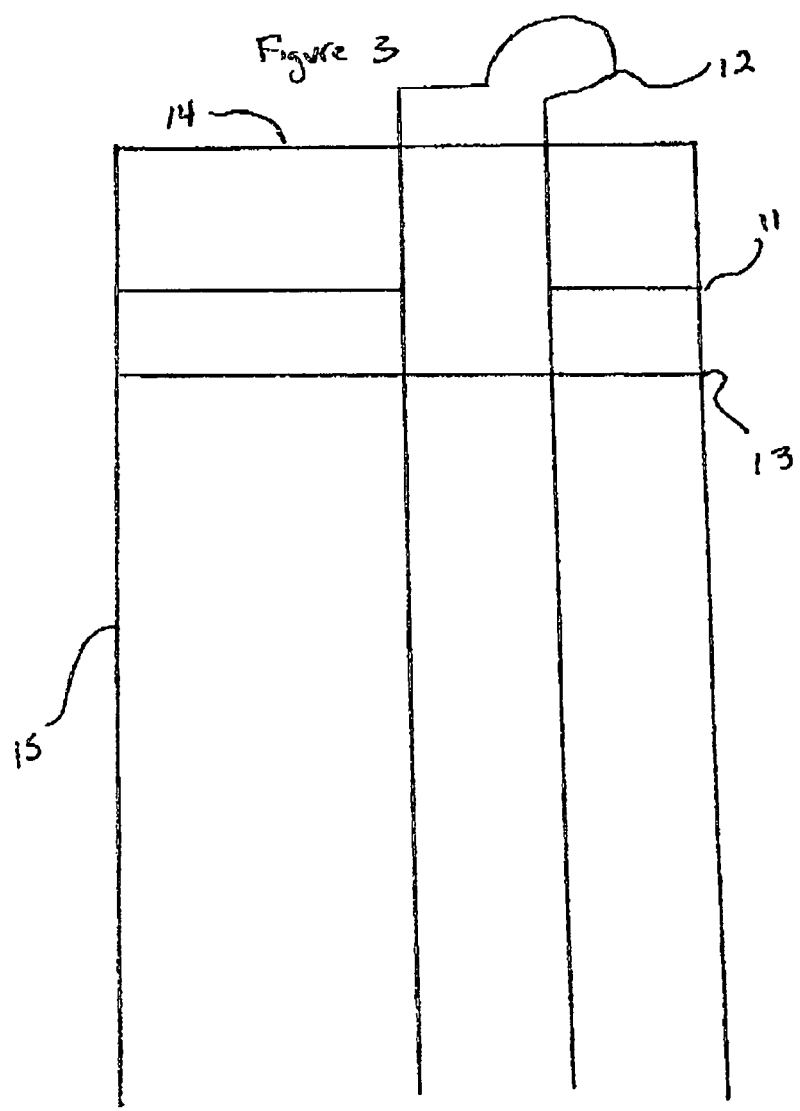
FIG. 3 is a perspective view of a flap for exposing stethoscope ear tubes according to an embodiment of the present invention.
Figure 4:
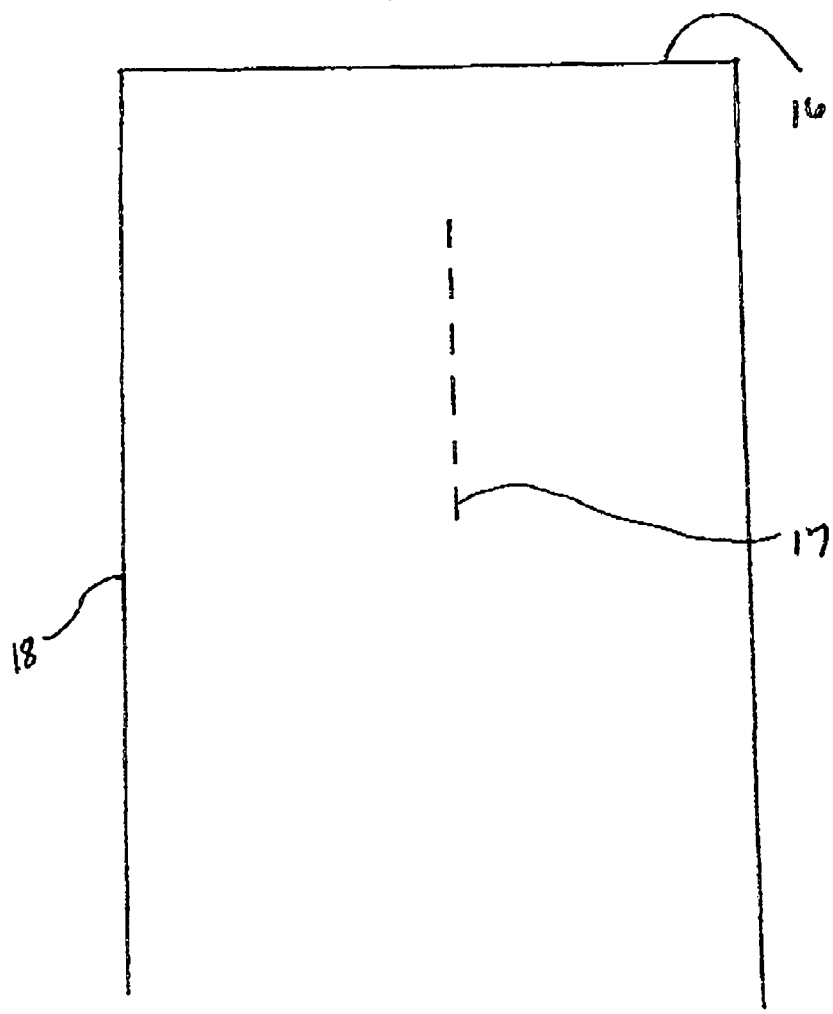
FIG. 4 is a perspective view of a tear line for exposing stethoscope ear tubes according to an embodiment of the present invention.
Figure 5:
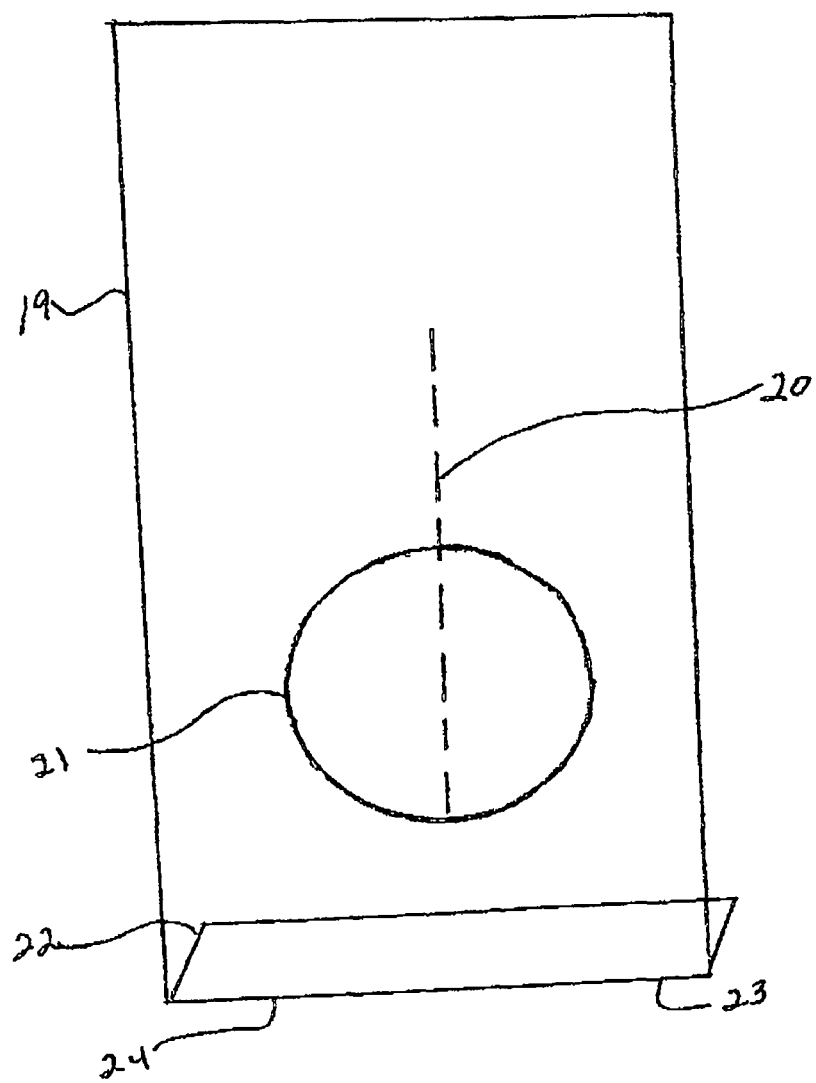
FIG. 5 is a perspective view of a tear line for exposing a stethoscope bell portion according to an embodiment of the present invention.

Numbers 1 and 2 are folds in which a stethoscope may or may not be exposed. The top of each tube piece numbered 3, 4, and 5 represent the sides that are permanently sealed. Number 6 is the opening that the stethoscope is fed through and number 7 represents a flap that folds under and over the stethoscope.

FIG. 2

Numbers 9 and 10 represent the fold that can be utilized when exposure of the ear pieces are needed. Number 8 and 11 are sides that are permanently sealed.

FIG. 3

Number 12 is the stethoscope ear piece while numbers 11 and 13 allow exposure of the ear piece. Number 14 and 15 are permanently sealed sides of the tubing.

FIG. 4

Back side of ear piece tubing with number 16 and 18 are permanently sealed and number 17 is a tear that may be used by tearing apart to expose the ear piece of the stethoscope.

FIG. 5

Front and back view of elongated bottom cover. Number 19 are the sides which are permanently sealed; number 20 is a tear line of the back side of the cover; number 21 represents the bell portion of a stethoscope; number 22 is the bottom flap on the back side which folds under and over the opening and number 23 is the opening in which a stethoscope is fed through.

FIGS. 6, 7 AND 8

Figure 6:
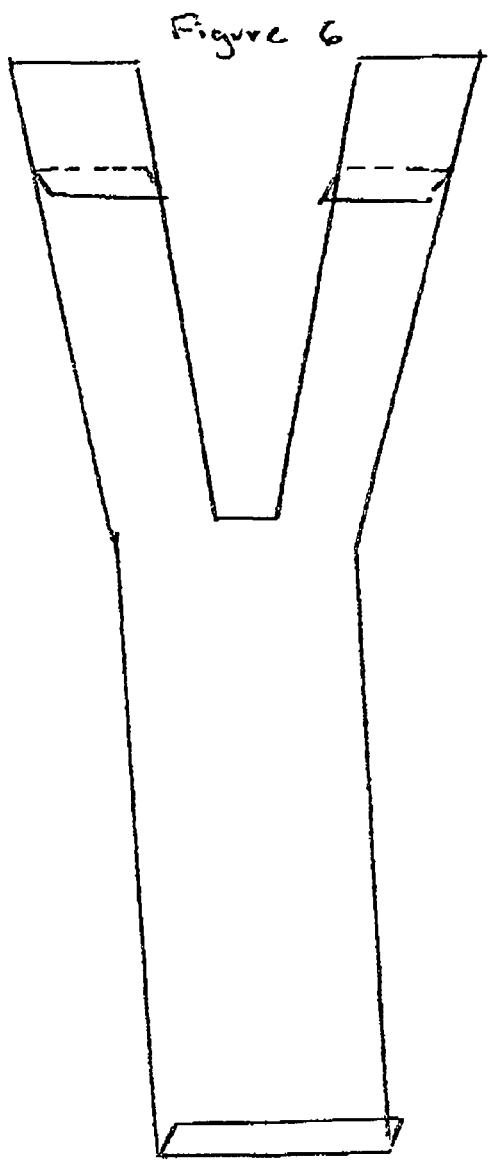
FIG. 6 is a perspective view of the disposable isolation/protective stethoscope cover according to an embodiment of the present invention.
Figure 7:
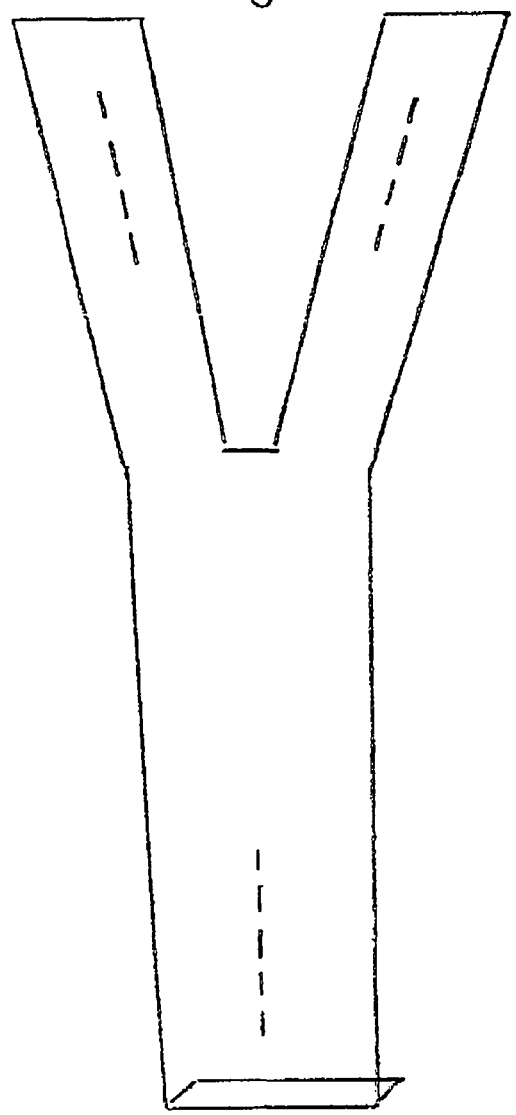
FIG. 7 is a perspective view of the disposable isolation/protective stethoscope cover according to an embodiment of the present invention.
Figure 8:
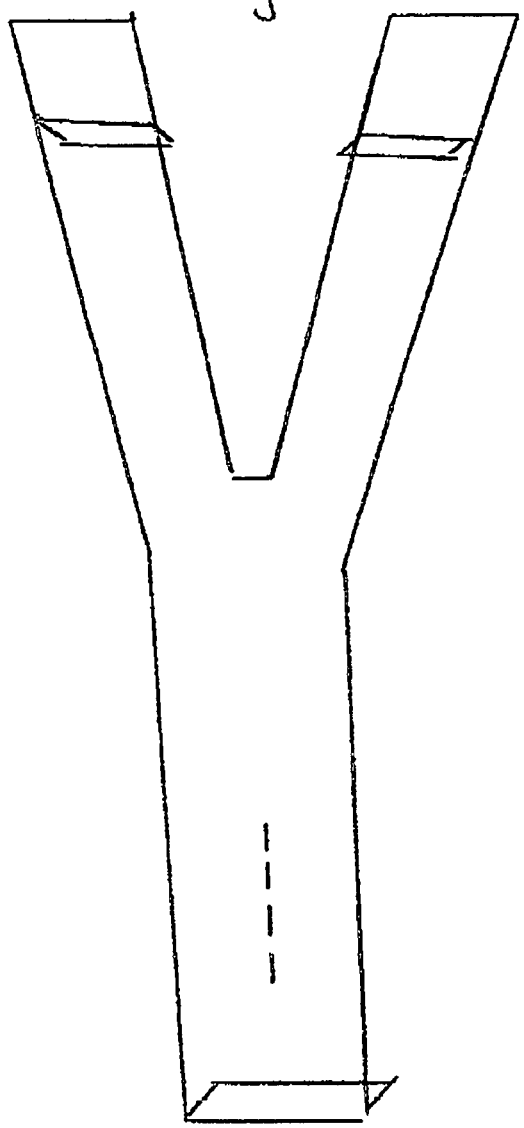
FIG. 8 is a perspective view of the disposable isolation/protective stethoscope cover according to an embodiment of the present invention.

FIG. 6 is Claim one cover; FIG. 7 is Claim two cover; FIG. 8 is claim 3 cover.

The invention claimed is:

1. A disposable isolation/protective cover for a stethoscope comprising: a bell receiving portion, an elongated connector body receiving portion and two ear piece tube receiving portions; wherein said isolation/protective cover is sealed on all sides except a bottom side defining the bell receiving portion and having an opening for permitting the stethoscope to be inserted therethrough; said cover material is selected from an OSHA approved material consisting of material impermeable viruses, bacteria and fluids; wherein the cover is sealed using an ultrasonic welding, adhesive bonding, radio-frequency sealing or heat sealing.

2. The disposable isolation/protective cover of claim 1, wherein each of said two ear piece tube receiving portions and said bell receiving portion have a vertical tear line on a back side of the cover which can be opened by pulling apart an appropriate tear line for clean use.

3. The disposable isolation/protective cover of claim 1, wherein each of said two ear piece tube receiving portions includes a flap which can be opened for exposure of stethoscope ear piece tubes for clean use, and wherein said bottom side opening of the cover includes a flap for closing said opening.

* * * * *